US00PP22263P2

(12) United States Plant Patent

Johnston et al.

(10) Patent No.: US PP22,263 P2

(45) Date of Patent: Nov. 22, 2011

(54) *GOMPHRENA* PLANT NAMED 'BALBOA'

(50) Latin Name: *Gomphrena leontopodioides*
Varietal Denomination: Balboa

(75) Inventors: Margaret Johnston, Toowoomba (AU); Dion Harrison, Karana Downs (AU); Daryl Joyce, Karalee (AU)

(73) Assignee: University of Queensland, St. Lucia, Queensland (AU)

( * ) Notice: Subject to any disclaimer, the term of this patent is extended or adjusted under 35 U.S.C. 154(b) by 0 days.

(21) Appl. No.: 12/804,008

(22) Filed: Jul. 12, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Gomphrena* plant named 'Balboa', characterized by its tall and upright plant habit; vigorous growth habit; freely branching habit; large grey green-colored leaves; and purple-colored flowers with a white lanulose-colored reverse giving a bi-color appearance to the flower.

1 Drawing Sheet

Botanical designation: *Gomphrena leontopodioides.*
Cultivar denomination: 'BALBOA'.

BACKGROUND OF THE INVENTION

The present invention relates to a new and distinct cultivar of *Gomphrena* plant, botanically known as *Gomphrena leontopodioides* and hereinafter referred to by the name 'Balboa'.

The new *Gomphrena* plant is a product of a breeding program that is focused on creating new upright and freely branching *Gomphrena* plants that propagate easily and have numerous attractive flowers.

The new *Gomphrena* plant was discovered and selected by the Inventors as a single flowering plant from within the progeny of a cross-pollination of two unidentified selections of *Gomphrena leontopodioides,* not patented, in a controlled environment in Gatton, Queensland, Australia on Apr. 19, 2007. The new *Gomphrena* plant was selected on the basis of its tall upright plant form, grey green-colored leaves and purple and white-colored flowers.

Asexual reproduction of the new *Gomphrena* plant by terminal cuttings in a controlled environment in Gatton, Queensland, Australia since Jul. 6, 2007, has shown that the unique features of this new *Gomphrena* plant are stable and reproduced true to type in successive generations.

SUMMARY OF THE INVENTION

Plants of the new *Gomphrena* have not been observed under all possible environmental conditions. The phenotype may vary somewhat with variations in environmental conditions such as temperature and light intensity without, however, any variance in genotype.

The following traits have been repeatedly observed and are determined to be the unique characteristics of 'Balboa'. These characteristics in combination distinguish 'Balboa' as a new and distinct *Gomphrena* plant:

1. Tall and upright plant habit.
2. Vigorous growth habit.
3. Freely branching habit.

4. Large grey green-colored leaves.
5. Purple-colored flowers with a white lanulose-colored reverse giving a bi-color appearance to the flower.

Plants of the new *Gomphrena* differ from plants of the parent selections primarily in the following characteristics:

1. Plants of the new *Gomphrena* are taller, more upright and more vigorous than plants of the parent selections.
2. Plants of the new *Gomphrena* are more freely branching and denser than plants of the parent selections.
3. Leaves of plants of the new *Gomphrena* are larger and more pubescent than leaves of plants of the parent selections.
4. Plants of the new *Gomphrena* and the parent selections differ in flower color as plants of the parent selections have purple pink and white-colored flowers.

Plants of the new *Gomphrena* can be compared to plants of *Gomphrena leontopodioides* 'Empress', not patented. In side-by-side comparisons conducted in Galton, Queensland, Australia, plants of the new *Gomphrena* differed from plants of 'Empress' in the following characteristics:

1. Plants of the new *Gomphrena* were taller than plants of 'Empress'.
2. Leaves of plants of the new *Gomphrena* were more pubescent than leaves of plants of 'Empress'.
3. Plants of the new *Gomphrena* flowered later than plants of 'Empress'.
4. Plants of the new *Gomphrena* and 'Empress' differed in flower color as plants of 'Empress' had purple pink-colored flowers.

BRIEF DESCRIPTION OF THE PHOTOGRAPHS

The accompanying colored photographs illustrate the overall appearance of the new *Gomphrena* plant showing the colors as true as it is reasonably possible to obtain in colored reproductions of this type. Colors in the photographs may differ slightly from the color values cited in the detailed botanical description which accurately describe the colors of the new *Gomphrena* plant.

The photograph at the bottom of the sheet comprises a side perspective view of typical flowering plants of 'Balboa' grown in a container.

The photograph at the top of the sheet is a close-up view of typical flowers of 'Balboa'.

DETAILED BOTANICAL DESCRIPTION

Plants used for the aforementioned photographs and following description were grown under conditions which closely approximate commercial production conditions during the spring with five plants in one-gallon containers in an outdoor nursery in Bonsall, Calif. During the production of the plants, day temperatures averaged 32° C. and night temperatures averaged 4° C. Plants were pinched three times and were six months old when the photographs and description were taken. In the following description, color references are made to The Royal Horticultural Society Colour Chart, 2007 Edition, except where general terms of ordinary dictionary significance are used.

Botanical classification: *Gomphrena leontopodioides* 'Balboa'.

Parentage:

*Female, or seed, parent.*—Unidentified selection of *Gomphrena leontopodioides,* not patented.

*Male, or pollen, parent.*—Unidentified selection of *Gomphrena leontopodioides,* not patented.

Propagation:

*Type.*—By terminal cuttings.

*Time to initiate roots, summer.*—About one to two weeks at 18° C. to 22° C.

*Time to initiate roots, winter.*—About three to four weeks at 18° C. to 22° C.

*Time to produce a rooted young plant, summer.*—About five weeks at 20° C. to 24° C.

*Time to produce a rooted young plant, winter.*—About six weeks at 20° C. to 24° C.

*Root description.*—Fine, fibrous; white in color.

*Rooting habit.*—Moderate branching; moderately dense.

Plant description:

*Plant and growth habit.*—Tall and upright plant habit; vigorous growth habit; freely branching habit; about five primary branches develop per plant each branching two to three times more; dense and bushy habit; pinching enhances lateral branch development.

*Plant height.*—About 32 cm.

*Plant diameter.*—About 14 cm by 19 cm.

Lateral branch description:

*Length.*—About 29 cm.

*Diameter.*—About 5.5 mm.

*Internode length, vegetative plants.*—About 1.5 cm.

*Internode length, reproductive plants.*—About 6.5 cm.

*Strength.*—Strong.

*Aspect.*—Upright to slightly outwardly.

*Texture.*—Densely covered with lanulose pubescence.

*Color.*—Close to 196D.

Foliage description:

*Arrangement.*—Vegetative plants, alternate; reproductive plants, opposite; vegetative and reproductive plants, simple and sessile.

*Length.*—About 7.8 cm.

*Width.*—About 7 mm.

*Shape.*—Lanceolate.

*Apex.*—Acute.

*Base.*—Clasping.

*Margin.*—Entire.

*Texture, upper and lower surfaces.*—Densely covered with lanulose pubescence.

*Venation pattern.*—Pinnate with one midvein and arcuate lateral veins.

*Color.*—Developing leaves, upper and lower surfaces: Close to 194B. Fully expanded leaves, upper and lower surfaces: Close to 148A; venation, close to 194A; white-colored dense lanulose pubescence gives a grey green-colored appearance to the fully expanded leaves.

Flower description:

*Flower arrangement and habit.*—Small and slender flowers arranged in dense terminal heads; freely flowering habit with about 32 flowers per inflorescence and about 12 to 15 inflorescences developing per plant; upright to outwardly-facing sessile flowers have a single five-parted perianth; flower heads subtended by two small leafy lanulose bracts.

*Fragrance.*—None detected.

*Natural flowering season.*—Plants flower during the spring and summer in Southern California; plants begin flowering about three to six months after planting.

*Flower longevity.*—Flowers last about four weeks on the plant; flowers persistent.

*Inflorescence height.*—About 1.8 cm.

*Inflorescence diameter.*—About 2.7 cm.

*Flower height.*—About 1.5 cm.

*Flower diameter.*—About 5 mm.

*Flower buds.*—Length: About 1.1 cm. Diameter: About 3 mm. Shape: Lanceolate. Color: Close to N78C.

*Perianth segments.*—Quantity/arrangement: Five segments in a single whorl. Shape: Lanceolate. Apex: Acute. Base: Truncate. Margin: Entire. Length: About 1.3 cm. Width: About 3 mm. Texture, upper surface: Smooth, glabrous; satiny. Texture, lower surface: Lanulose pubescence. Color: When opening, upper surface: Close to N78C. When opening, lower surface: Close to NN155D. Fully opened, upper surface: Close to N78C; narrow dark central stripe, close to 200B; color does not fade with development. Fully opened, lower surface: Close to NN155D.

*Sepals.*—None observed.

*Bracts.*—Quantity/arrangement: Two subtending the flower head. Length: About 5 mm. Width: About 2.5 mm. Shape: Lanceolate. Apex: Acute. Texture, upper and lower surfaces: Lanulose pubescence. Color, upper and lower surfaces: Whitish due to pubescence.

*Peduncles.*—Length: About 7.5 cm. Diameter: About 2 mm. Angle: Mostly upright to 40° from vertical. Strength: Strong. Texture: Lanulose pubescence. Color: Close to 196C to 196D.

Reproductive organs:

*Stamens.*—Quantity/arrangement: Five per flower; filaments united in a cylindrical tube enclosing the gynoecium. Filament length: About 1.1 cm. Filament color: Close to NN155D. Anther shape: Oval. Anther length: About 1 mm. Anther color: Close to 21C. Pollen amount: Scarce. Pollen color: Close to 23A.

*Pistils.*—Quantity: One per flower. Pistil length: About 1.1 cm. Style length: About 6 mm. Style color: Close to N78B. Stigma shape: Bi-parted. Stigma color: Close to N78A. Ovary color: Close to N78B to N78C.

*Seed/fruit.*—Seed and fruit development have not been observed on plants of the new *Gomphrena.*

Pathogen/pest resistance: Plants of the new *Gomphrena* have not been observed to be resistant to pests and pathogens common to *Gomphrena* plants.

Garden performance: Plants of the new *Gomphrena* have been observed to have good garden performance and to tolerate wind, rain and temperatures ranging from about 1° C. to 35° C.

It is claimed:

1. A new and distinct *Gomphrena* plant named 'Balboa' as illustrated and described.

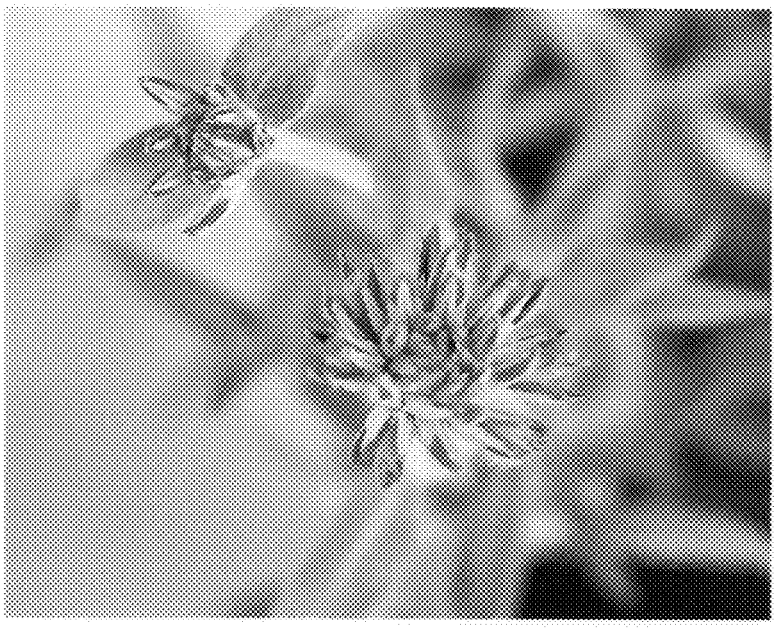
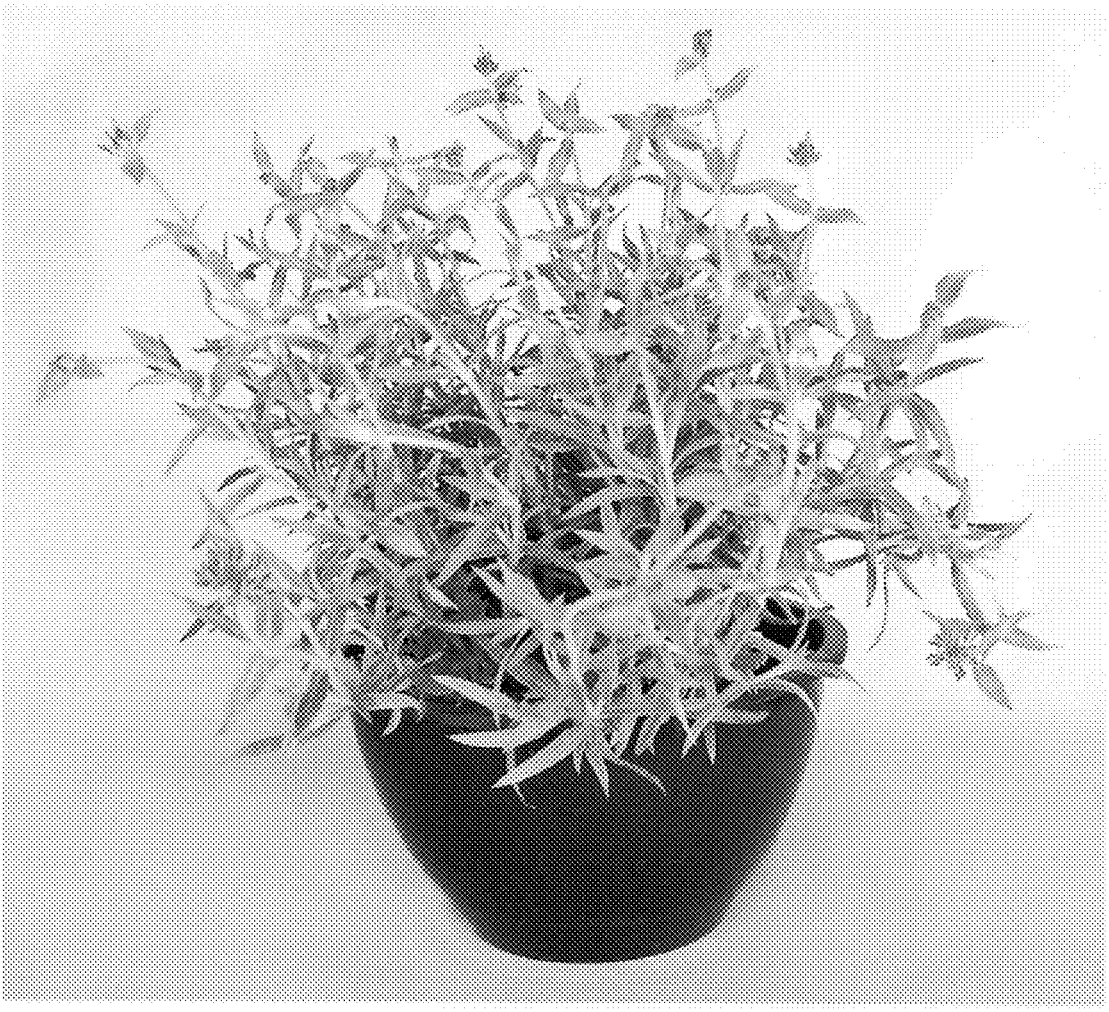

* * * * *